United States Patent
Banks

(10) Patent No.: US 8,328,845 B2
(45) Date of Patent: Dec. 11, 2012

(54) SAFETY TWEEZERS

(76) Inventor: Debra L. Banks, Audlem (GB)

( * ) Notice: Subject to any disclaimer, the term of this patent is extended or adjusted under 35 U.S.C. 154(b) by 451 days.

(21) Appl. No.: 12/467,349

(22) Filed: May 18, 2009

(65) Prior Publication Data

US 2010/0280544 A1 Nov. 4, 2010

(30) Foreign Application Priority Data

May 4, 2009 (EP) .......................... 001118004-0001

(51) Int. Cl.
*A61B 17/50* (2006.01)
*A61B 17/00* (2006.01)

(52) U.S. Cl. ................... 606/210; 606/205; 606/199

(58) Field of Classification Search .............. 606/199, 606/205, 210
See application file for complete search history.

(56) References Cited

U.S. PATENT DOCUMENTS

| 420,125 | A | * | 1/1890 | Swain | 294/99.2 |
| 4,389,912 | A | * | 6/1983 | Dallons et al. | 81/320 |
| 4,442,837 | A | | 4/1984 | Keatley | |
| 4,457,756 | A | | 7/1984 | Kern et al. | |
| 5,972,021 | A | * | 10/1999 | Huttner et al. | 606/210 |

FOREIGN PATENT DOCUMENTS

| EP | 0237589 A1 | 9/1987 |
| JP | 2004042147 | 2/2004 |
| JP | 2004042147 A | 2/2004 |
| JP | 2005013639 A | 1/2005 |
| JP | 2005125032 | 5/2005 |
| JP | 2006136699 | 6/2006 |
| JP | 2007054573 A | 3/2007 |
| NL | 1006517 | 1/1999 |
| NL | 1006517 C2 | 12/1999 |
| WO | 98/01096 A1 | 1/1998 |
| WO | WO 03/035144 | 1/2003 |
| WO | 2007121238 A2 | 10/2007 |
| WO | WO 2007/121238 | 10/2007 |

OTHER PUBLICATIONS

Dornfest, Asha. "Use tweezers to grab crusty boogers." www.parenthacks.com. Oct. 1, 2007. <http://www.parenthacks.com/2007/10/use-tweezers-to.html>.*

(Continued)

*Primary Examiner* — Gary Jackson
*Assistant Examiner* — Kevin Everage
(74) *Attorney, Agent, or Firm* — Bradley D. Crose; Crose Law LLC

(57) ABSTRACT

An improved device and method for the removal of objects from orifices is provided; a pair of tweezers comprising two arms, each arm having a distal end and a proximate end, the arms being connected together at their proximate ends, either or both arms including stop means for limiting a depth of insertion of either or both distal end into an orifice; and, a method of removing mucus from a nostril, including the steps of providing a pair of tweezers comprising two arms, each arm having a distal end and a proximate end, the arms being connected together at their proximate ends, either or both arms including stop means for limiting a depth of insertion of either or both distal end into an orifice; inserting the distal ends of the arms into a nostril; gripping said mucus by the squeezing together of said arms; and withdrawing said tweezers from said nostril.

8 Claims, 6 Drawing Sheets

OTHER PUBLICATIONS

Serial No. GB 0722670.7 UK Intellectual Property Office, Search Report dated Sep. 10, 2008, 1 page.
Web page http://rainorshine.wordpress.com/2007/08/15/booger-removal-for-dummies/ "pigeon booker tweezer", dated Apr. 14, 2008, 1 page.
IPO Examination Report, Sep. 5, 2011.
IPO Examination Report, Apr. 26, 2011.
http://rainorshine.wordpress.com/2007/08/15/booger-removal-for-dummies/, Aug. 15, 2007.

* cited by examiner

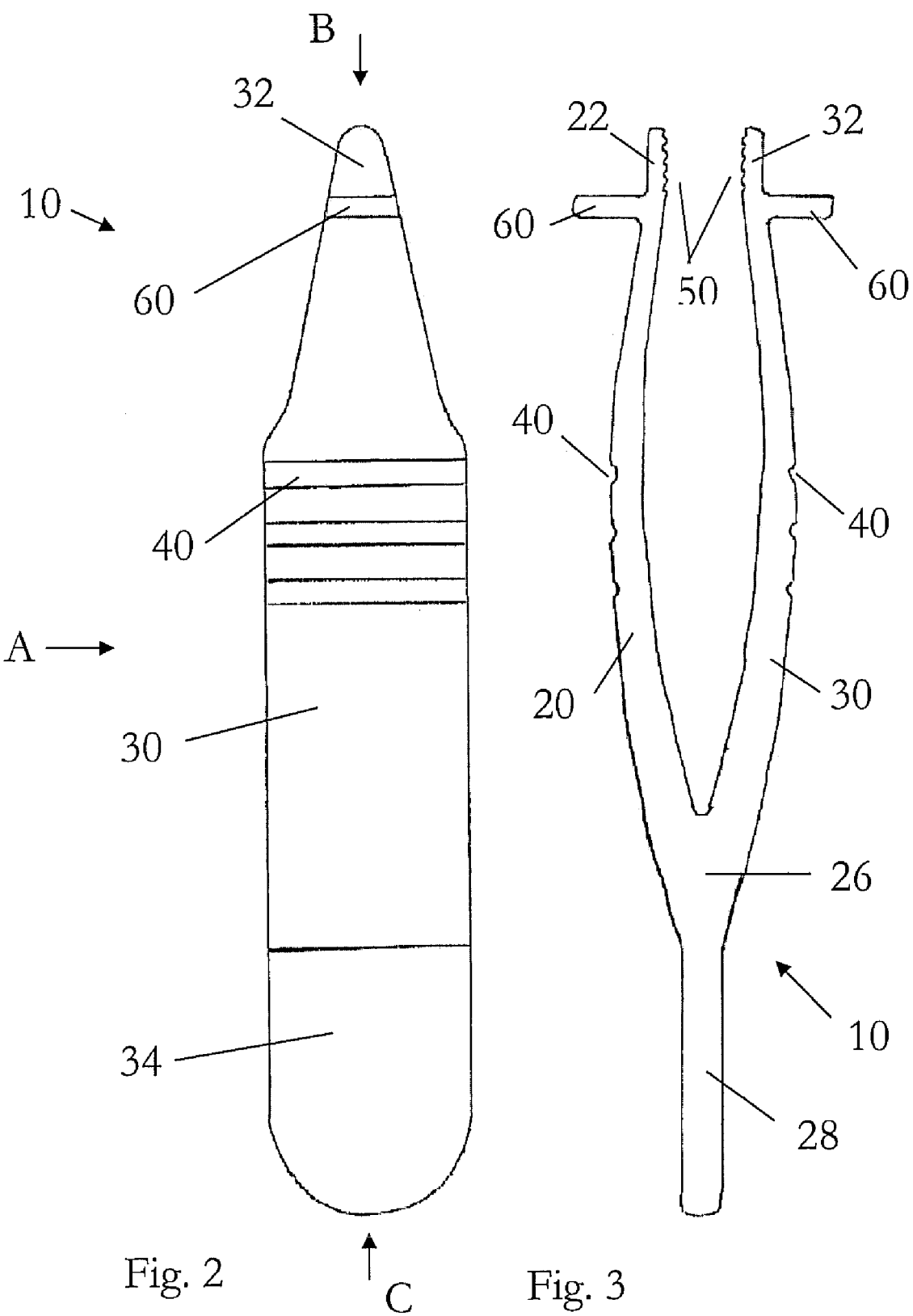

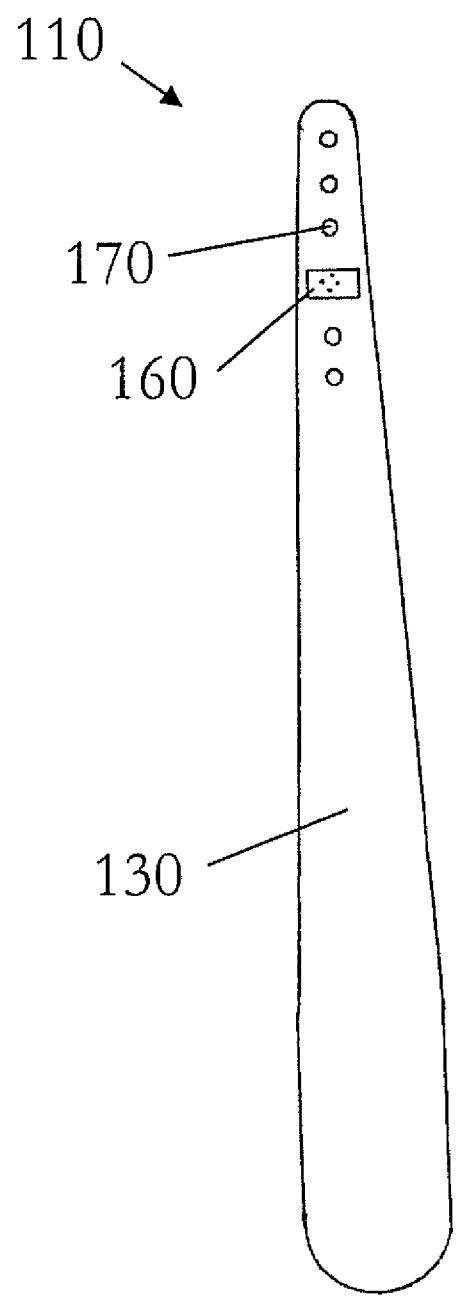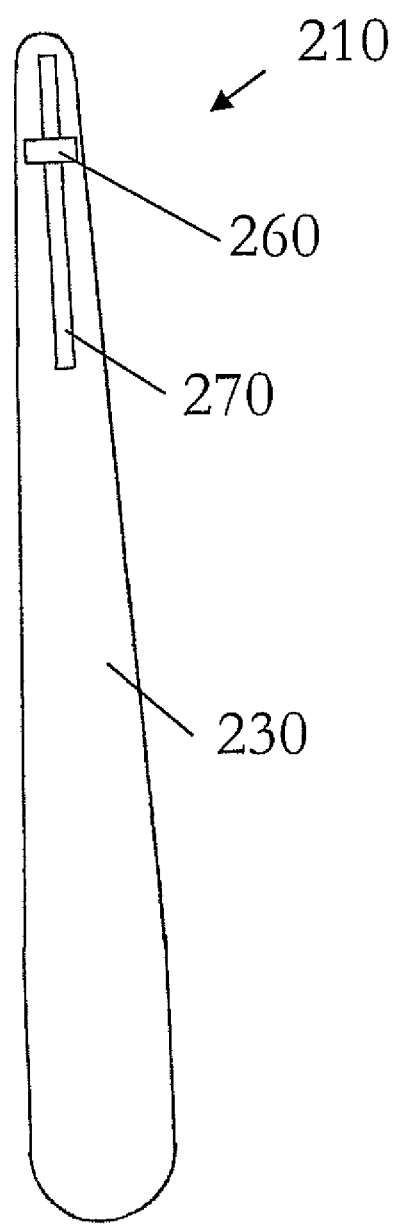
Fig. 7
Fig. 8

SAFETY TWEEZERS

CROSS REFERENCE TO RELATED APPLICATIONS

This application relates to and claims priority from OHIM 001118004-0001 filed May 5, 2009, under §119 and §172, the entire contents of which are herein incorporated fully by reference.

FIGURE FOR PUBLICATION

FIG. 1

BACKGROUND OF THE INVENTION

1. Field of the Invention

The present invention relates to safety tweezers and to a method of safely removing bodily excretions. In particular, although not exclusively, the present invention relates to a pair of tweezers for the use of removing dried mucus from babies' nostrils.

2. Description of the Related Art

Mucus naturally collects in nostrils. Able-bodied people may remove this mucus by the blowing of their nose. However, some people, such as infants, cannot perform this task which thus makes breathing difficult. This can make sleeping and feeding difficult.

To overcome this, aspirators are known which a cater may use to clear the nostril(s) of the sufferer. It comprises of a tube which is used to suck out the mucus, the carer providing the vacuum with their own mouths and a filter acting to prevent any of the removed mucus from entering the mouth of the carer. An example of such a device is described in EP-A1-1474186.

Another method to remove mucus is by the use of a pair of tweezers such as described in JP-A-2005125032. This entails the insertion of both of the distal ends of the tweezers into the nostril, gripping the mucus between the distal ends and withdrawing them. However, it is relatively easy for the person holding the tweezers to push the distal ends too far into the nostril thus causing damage to the inside of the nose and distress to the infant.

ASPECTS AND SUMMARY OF THE INVENTION

According to at least one alternative and adaptive embodiment of the invention, a pair of tweezers comprises two arms, each arm having a distal end and a proximate end, the arms being connected together at their proximate ends, either or both arms including stop means for limiting a depth of insertion of either or both distal end into an orifice.

According to another alternative and adaptive embodiment of the invention, there is provided a method of removing mucus from a nostril, includes the steps of providing a pair of tweezers comprising two arms, each arm having a distal end and a proximate end, the arms being connected together at their proximate ends, either or both arms including stop means for limiting a depth of insertion of either or both distal end into an orifice; inserting the distal ends of the arms into a nostril; gripping said mucus by the squeezing together of said arms; and withdrawing said tweezers from said nostril.

The present invention relates to an improved device and method for the removal of objects from orifices is provided; a pair of tweezers comprising two arms, each arm having a distal end and a proximate end, the arms being connected together at their proximate ends, either or both arms including stop means for limiting a depth of insertion of either or both distal end into an orifice; and, a method of removing mucus from a nostril, including the steps of providing a pair of tweezers comprising two arms, each arm having a distal end and a proximate end, the arms being connected together at their proximate ends, either or both arms including stop means for limiting a depth of insertion of either or both distal end into an orifice; inserting the distal ends of the arms into a nostril; gripping said mucus by the squeezing together of said arms; and withdrawing said tweezers from said nostril.

BRIEF DESCRIPTION OF THE DRAWINGS

FIG. 2 is a side view of the pair of tweezers of FIG. 1.

FIG. 3 is an alternative side view of the pair of tweezers of FIG. 1.

FIGS. 7 and 8 are side views of tweezers according to other embodiments of the invention.

BRIEF DESCRIPTION OF EMBODIMENTS OF THE INVENTION

Embodiments of the present invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 1:
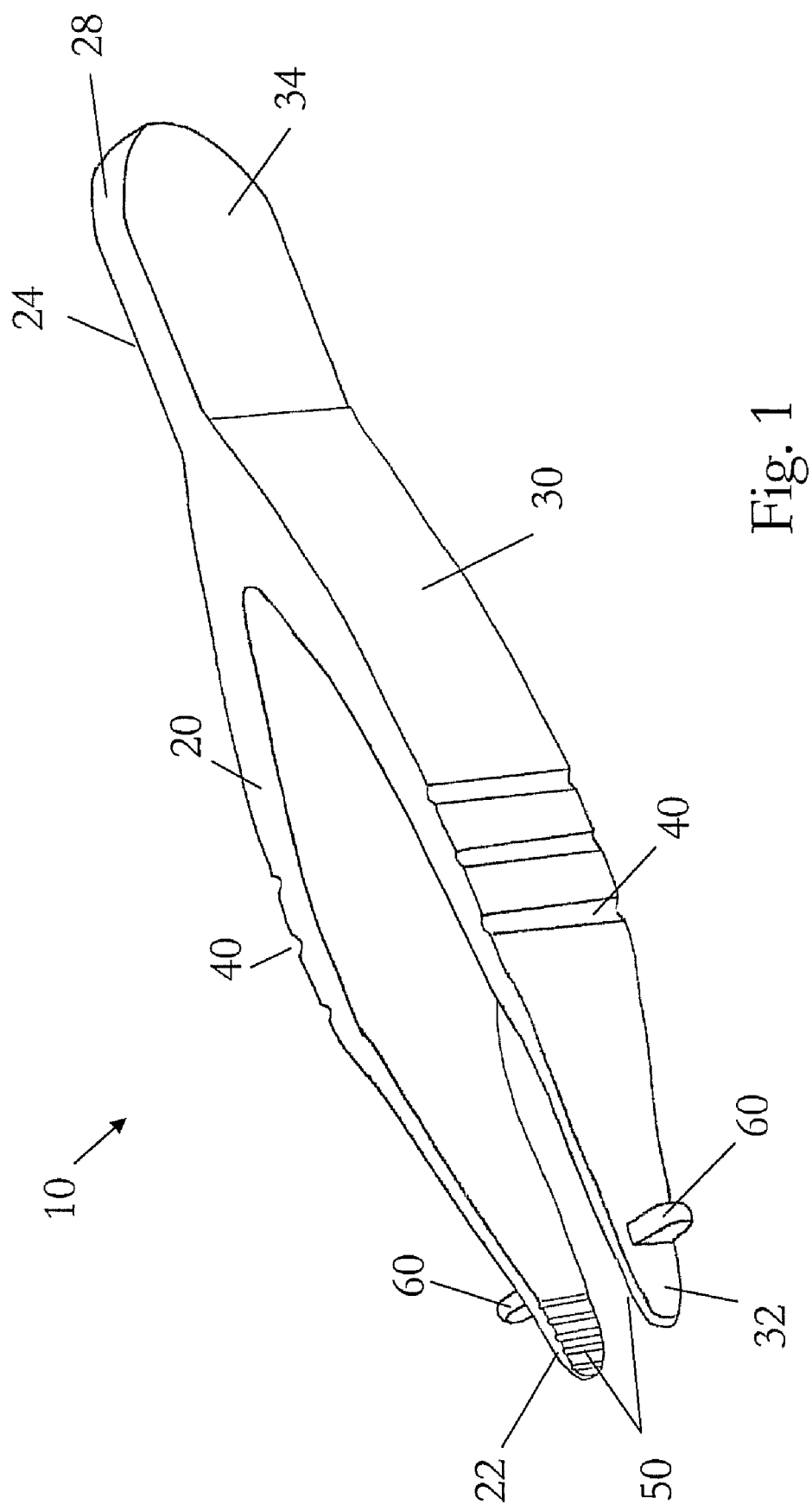
FIG. 1 is a perspective view of a pair of tweezers according to one embodiment of the invention.

As illustrated in FIG. 1 the tweezers 10 are comprised of two arms 20, 30. Each arm 20, 30 has a distal end 22, 32 and a proximate end 24, 34. The proximate ends 24, 34 of the arms 20, 30 are connected together to form the proximate end 28 of the tweezers. The two arms 20, 30 are shown at rest. However, pressure applied on the arms 20, 30 may move them inwardly towards one another such that the distal ends 22, 32 may be used to grip objects therebetween. When the pressure is released the arms 20, 30 will spring back to their at-rest position illustrated in FIG. 1. In other words, the arms 20, are resiliently connected together and require an external urging force to operate. In one embodiment, the two arms 20, 30 may be formed as one such that the proximate end 28 is unitary. This may be the case where the tweezers are formed from plastics for instance.

The two arms 20, 30 each include a gripping portion 40 which is formed of grooves in the outer surface of the arms. These may improve the gripping of the tweezers by a user in use. Furthermore, the distal end 22, 32 of each arm 20, 30 includes grooves on its inner surface. These may improve the gripping of objects by the tweezers in use. In other embodiments (not shown), the two arms 20, 30 may each include a gripping portion 40 which is formed of ridges in the outer surface of the arms, and/or the distal end 22, 32 of each arm 20, 30 may include ridges on its inner surface.

The distal end 22, 32 of each arm is rounded and/or blunted. This helps prevent injury to a person in use.

Each arm 20, 30 includes stop means in the form of a wing or tab 60 located on the outer surface and towards the distal ends 22, 32. They extend outwardly from the arms 20, 30 and act to limit the extent to which the distal ends 22, 32 of the tweezers 10 may be inserted into an orifice in use.

The wings or tabs 60 may be formed integrally with the arms 20, 30 or may be formed separately and connected to the arms 20, 30. They are located in this embodiment approximately 4 mm (0.16 inches) from the distal ends 22, 32 measured along the longitudinal length of each arm 20, 30. However, in other embodiments, the location may be different as will be discussed in later detail.

The length of each tab or wing 60, measured perpendicularly to the longitudinal lengths of the arms 20, 30, lies in the range 4 mm to 10 mm (0.16 to 0.39 inches). This is the length that each tab or wing 60 extends radially outwardly from the arms 20, 30. In this regard, the term "inner" refers to the direction of movement of the two arms 20, 30, in use, being squeezed together, and the term "outer" refers to the direction of movement of the two arms 20, 30 when released. The outer surface of each wing or tab 60 may be rounded.

The tweezers 10 may be used for insertion into a nostril to remove dried mucus. The tweezers 10 may also be used with other orifices such as ears for the removal of ear wax or unwanted hairs.

The tweezers 10 are illustrated in FIG. 2 in side view such that only one arm 30 is visible, the other arm 40 being hidden from view by arm 30. The arm 30 comprises a proximate end 34 and a distal end 32. A wing or tab 60 projects outwardly (out of the plane in which the longitudinal arm lies and towards the viewer of the Figure) from the distal end 32 of the arm 30. Three parallel grooves 40 are provided on the arm 30 to improve the gripping thereof. The illustration in FIG. 2 may be called a side-view.

The same tweezers 10 are illustrated in FIG. 3 as viewed in the direction of the arrow referenced "A" in FIG. 2. This may be called the top-view. The tweezers 10 comprise a left arm 20 and a right arm 30. The arms are connected together 26 to form the proximate end 28 of the tweezers 10. Both arms 20, 30 have a distal end 22, 32 respectively. A wing or tab 60 projects outwardly from the distal end 22, 32 of each arm 20, 30. These act, in use, to limit the depth of insertion of the distal end 22, 32 of the tweezers 10 into an aperture. The inside edge of each distal end 22, 32 of each arm 20, includes grooves 50 for improving the grip of objects therebetween.

Figure 4:
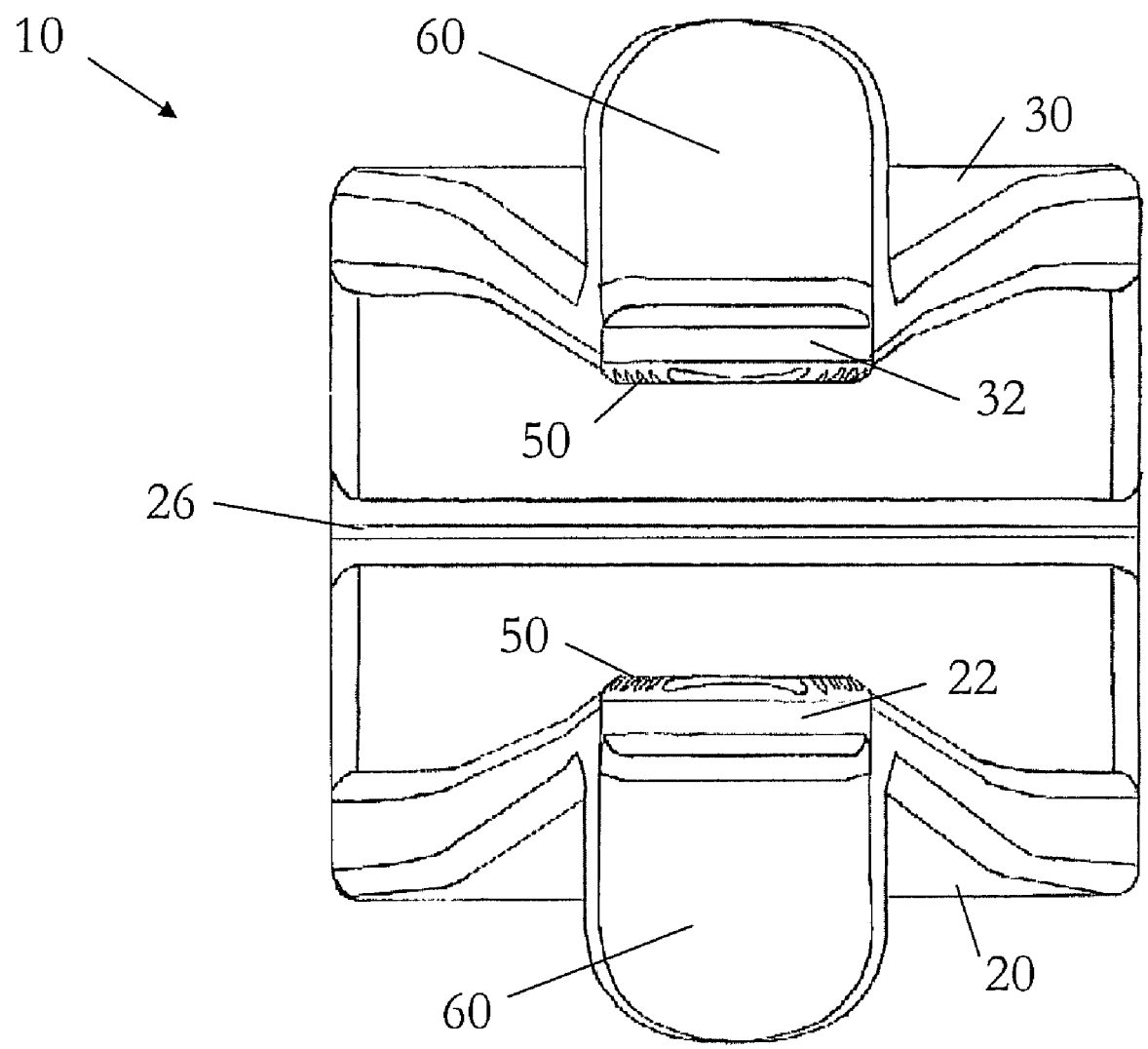
FIG. 4 is an end view of the pair of tweezers of FIG. 1.

The same tweezers 10 are illustrated in FIG. 4 as viewed in the direction of the arrow referenced "B" in FIG. 2. This may be called an end-view or front-view. The tweezers 10 comprise an upper arm 30 and a lower arm 20. The arms are connected together 26 to form the proximate end of the tweezers 10. Both arms 20, 30 have a distal end 22, 32 respectively. A wing or tab 60 projects outwardly from the distal end 22, 32 of each arm 20, 30, such that a wing or tab 60 projects upwardly from arm 30 and a wing or tab 60 projects downwardly from arm 20. These act, in use, to limit the depth of insertion of the distal end 22, 32 of the tweezers 10 into an aperture. The inside edge of each distal end 22, 32 of each arm 20, 30 includes grooves 50 for improving the grip of objects therebetween.

Figure 5:
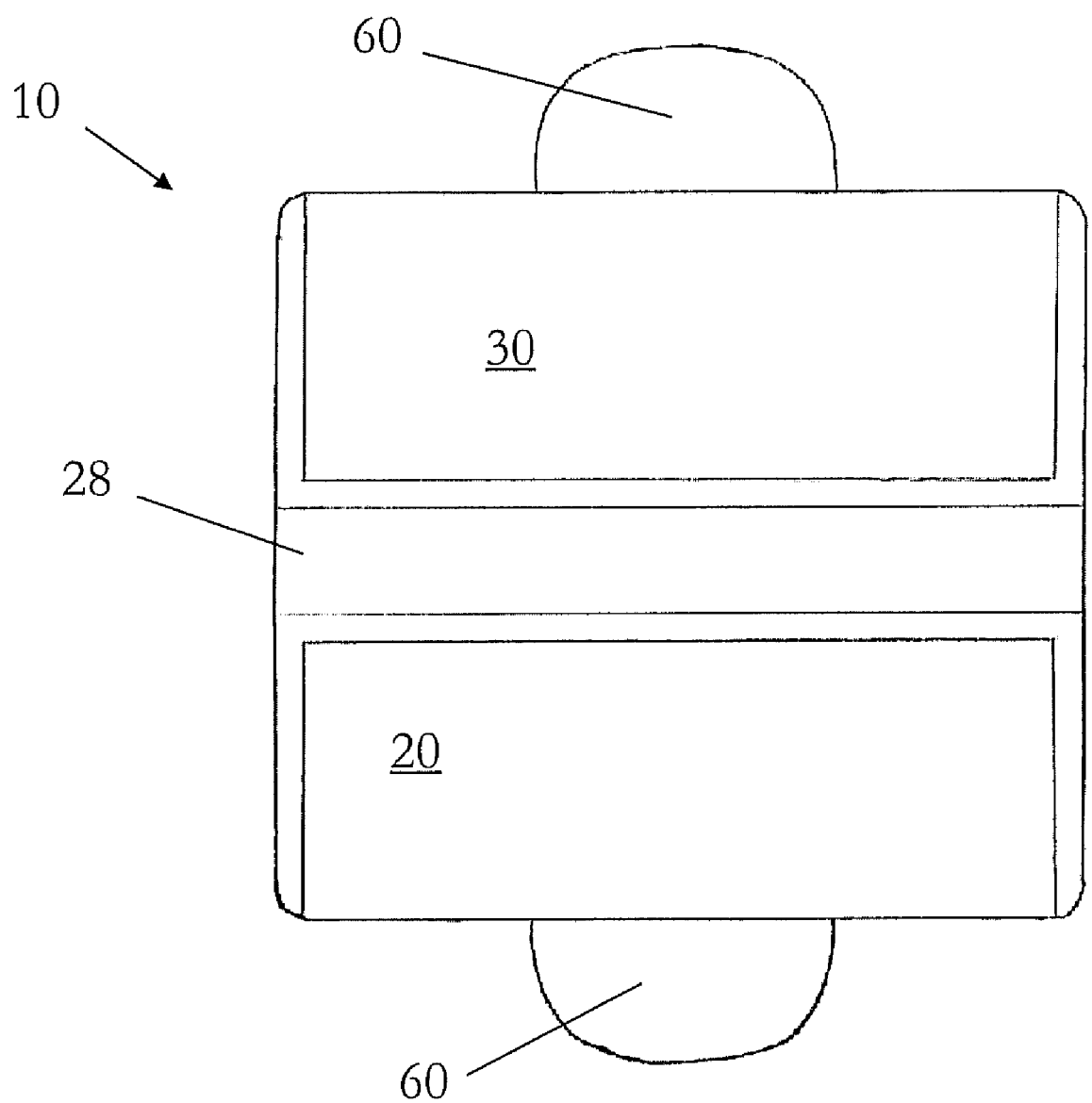
FIG. 5 is an opposite end view of the pair of tweezers of FIG. 4.

The same tweezers 10 are illustrated in FIG. 5 as viewed in the direction of the arrow referenced "C" in FIG. 2. This may be called an alternative end-view or rear-view. The tweezers 10 comprise an upper arm 30 and a lower arm 20. The arms are connected together to form the proximate end 28 of the tweezers 10. Both arms 20, 30 have a distal end respectively. A wing or tab 60 projects outwardly from the distal end of each arm 20, 30 such that a wing or tab 60 projects upwardly from arm 30 and a wing or tab 60 projects downwardly from arm 20. These act, in use, to limit the depth of insertion of the distal end of the tweezers 10 into an aperture.

Figure 6:
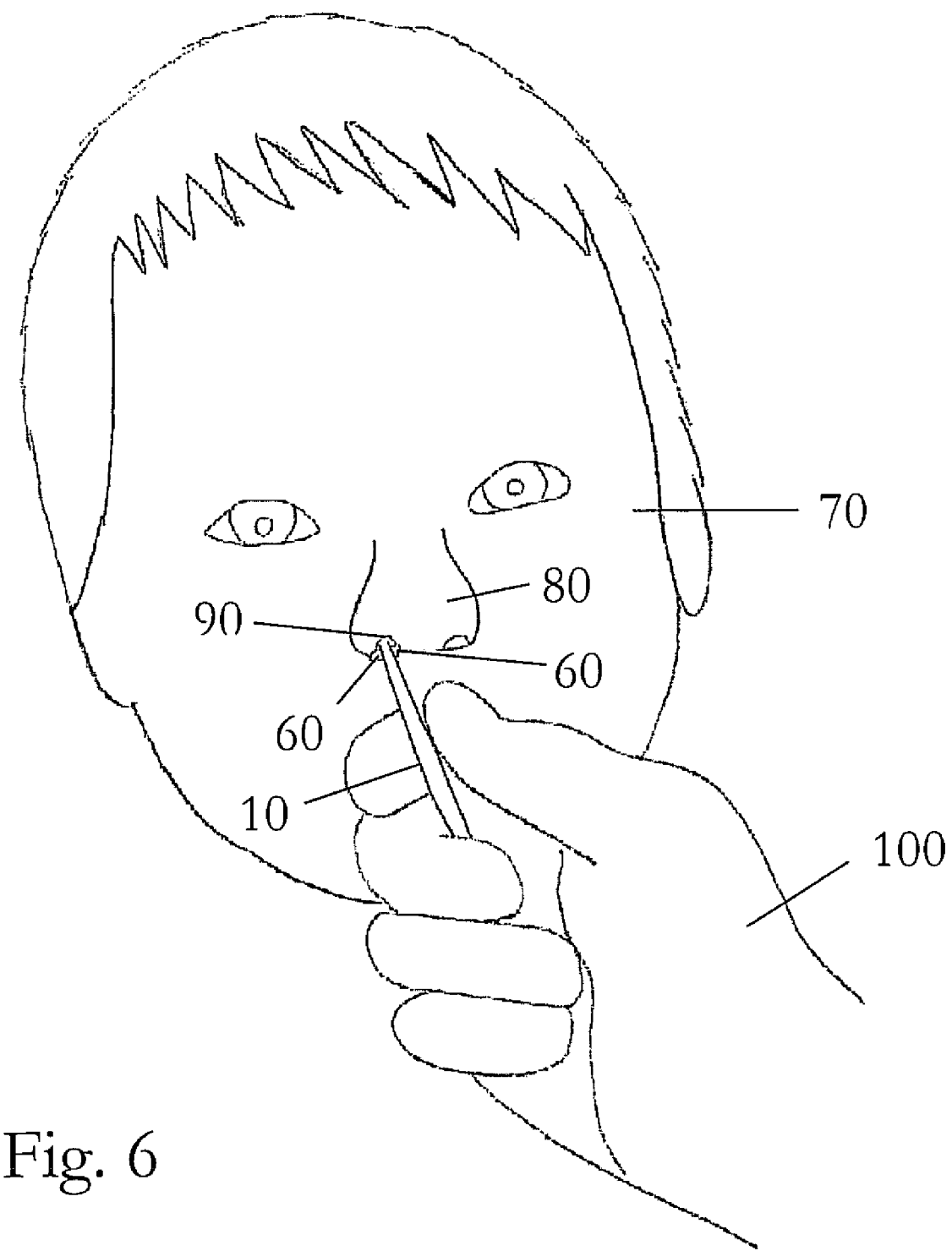
FIG. 6 is a perspective view of the tweezers of FIG. 1 being inserted into the nostril of an infant.

As illustrated in FIG. 6, the tweezers 10 may be used with an infant's 70 nose 80. The nose 80 has two nostrils 90. The tweezers 10 are being gripped by a user's hand 100 such that the proximate end is towards the user and the distal end is towards the infant 70. The distal end of each arm of the tweezers 10 is being inserted into the left nostril 90 as shown in the figure. The wings or tabs 60 are limiting the extent or depth to which the distal ends of the arms may be inserted into the nostril 90. This is because the wings or tabs 60 extend radially away from the length of the arms and are thus unable to fit inside the nostril 60 as the width of the tweezers 10, as measured at the point where the wings or tabs 60 extend outwardly from the arms, is greater than the width of the nostril 90.

With the tweezers 10 inserted into the nostril 90, any dried mucus or other object, may be gripped between the distal ends and removed without damage or injury to the child's (or other patient's) nose and without risk of over penetration into the nostrils as may be dictated by a medical professional Although illustrated in use with an infant 70 the tweezers 10 may be used with a person of any age. They may also be used with animals.

The tweezers 10, 110, 210 may be formed of plastics, and/or metals, and/or other materials.

The wings or tabs 60, 160, 260 may be provided along the sides of the arms such that they extend radially in the same plane as the grooves 40 illustrated in FIG. 1.

A different adaptive and alternative embodiment of the tweezers 110 is illustrated in FIG. 7. This embodiment differs from the embodiment illustrated in FIG. 1 in that the location of the wings or tabs 160 relative to the distal ends of each arm may be adjusted. This is effected by the provision of stop means location adjustment means. In this embodiment the stop means location adjustment means takes the form of a series or row of holes 170 provided in the outer surface of each arm. The stop means or wings or tabs 160 include a peg (not shown) which may be inserted into any one of the holes 170. Alternatively, but not shown, the arms may include a row of pegs and the wings or tabs include a hole, slot, or gap for connection therewith. In this way a user may choose the location of the tabs or wings 160 relative to the distal ends of the tweezers 110 and thus selectively limiting during use the extent or depth of insertion of the distal ends of the tweezers 110 into the orifice. As a non-restrictive estimate for illustrative purposes only, the wings or tabs 160 may be located in the range 1 to 15 mm (0.04 to 0.60 inches) measured from the distal end of each arm in the longitudinal direction.

An alternative embodiment of the tweezers 210 is illustrated in FIG. 8. This embodiment differs from the embodiment illustrated in FIG. 1 in that the location of the wings or tabs 260 relative to the distal ends of each arm may be slot-adjusted. This is affected by the provision of stop means location adjustment means. In this embodiment the stop means location adjustment means takes the form of a slot 270 provided in the outer surface of each arm. The stop means or wings or tabs 260 include a male member (not shown) which slidingly fits in the slot 270. This male member retains the wings or tabs 60 in the slot 270 but allows it to be slidably moved along and relative to the slot relative to the longitudinal length of the arms. This movement allows adjustment of their location relative to the distal ends of the tweezers 210. In this way a user may choose the location of the tabs or wings 260 relative to the distal ends of the tweezers 210 and thus selectively limit the extent or depth of insertion of the distal ends of the tweezers 210 into the orifice. This embodiment also provides the benefit of preventing unintended separation of the wings or tabs 260 from tweezers 210, and unintended loss of the wings which may pose a choking hazard for young children. As an additional benefit, the proposed stop means location adjustment means is infinitely adjustable relative to slot 270 on opposing sides of tweezers 210, such that an adjustment on one tweezers arm may be adjusted to a different position or location relative to the distal ends of tweezers 210, than a position on the corresponding tweezers arm, thereby allowing for non-parallel adjustment and adaptation to differing angular arrangements—so the tweezers 210 may be held at an angle to a nostril opening while still reaching into and employing the stop means.

It will be understood that when an element is referred to as being "connected to" another element, it can be directly connected or coupled to the other element or intervening elements may be present. As used herein, the term "and/or" includes any and all combinations of one or more of the associated listed items. In the figures, the thickness and/or sizes of certain lines, layers, components, elements or features may be exaggerated for clarity and/or may not be drawn to scale.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Embodiments of the invention may be described herein with reference to illustrations that are schematic illustrations of idealized embodiments of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein. In the drawings and specification, there have been disclosed typical embodiments of the invention and, although specific terms are employed, they are used in a generic and descriptive sense only and not for purposes of imitation, the scope of the invention being set forth in the following claims.

The invention claimed is:

1. A pair of tweezers comprising two arms, each arm having a distal end and a proximate end, the arms being connected together at their proximate ends, at least one of said arms including stop means for limiting a depth of insertion of either or both distal end(s) into a nostril during a use thereof; at least one location adjustment means for enabling the position of the stop means to be adjustable relative to the distal ends of the arms, wherein the stop means further comprise a wing or tab on an outer side surface of either or both said arms; wherein the distal ends of each arm are rounded, thereby minimizing a risk of injury to said orifice during said use, and said stop means are located approximately 4 mm from the distal end of respective said arms.

2. The pair of tweezers according to claim 1 wherein said arms have opposing inner surfaces; said inner surfaces of said distal ends of arms including a gripping surface to improve a gripping of external objects for removal from said nostril during said use.

3. The pair of tweezers according to claim 2 wherein said arms have outer surfaces and said outer surfaces of either or both arms include a gripping surface to improve the gripping of the tweezers by a user.

4. The pair of tweezers according to claim 1 wherein the inner surfaces of the distal ends of either or both arms include a gripping surface to improve the gripping of objects.

5. The pair of tweezers according to claim 1 wherein the outer surfaces of either or both arms include a gripping surface to improve the gripping of the tweezers by a user.

6. The pair of tweezers according to claim 1 wherein the tweezers are comprised of plastics.

7. A method of removing mucus from a nostril, comprising the steps of:
    a. providing a pair of tweezers comprising two arms, each arm having a distal end and a proximate end, the arms being connected together at their proximate ends, either or both arms including stop means for limiting a depth of insertion of either or both distal end into a nostril; the stop means comprising a wing or tab on an outer side surface of either or both said arms, the distal ends of each arm being rounded, thereby minimizing a risk of injury to said nostril during said use; and said stop means being located approximately 4 mm from the distal end of respective said arms;
    b. inserting the distal ends of the arms into a nostril;
    c. gripping said mucus by the squeezing together of said arms; and
    d. withdrawing said tweezers from said nostril.

8. The method of removing mucus from a nostril according to claim 7 wherein the nostril is an infant's nostril.

* * * * *